(12) United States Patent
Ahn (10) Patent No.: US 10,524,839 B2
(45) Date of Patent: Jan. 7, 2020

(54) BONE FIXATION SCREW APPARATUS AND FASTENING METHOD THEREOF

(71) Applicants: GBS Commonwealth Co., Ltd., Seoul (KR); PMT Republic, Inc., Walnut, CA (US)

(72) Inventor: Kyung Ki Ahn, Seoul (KR)

(73) Assignees: GBS COMMONWEALTH CO., LTD., Seoul (KR); PMT REPUBLIC, INC., Walnut, CA (US)

( * ) Notice: Subject to any disclaimer, the term of this patent is extended or adjusted under 35 U.S.C. 154(b) by 0 days.

(21) Appl. No.: 16/068,773

(22) PCT Filed: Sep. 25, 2017

(86) PCT No.: PCT/KR2017/010550
§ 371 (c)(1),
(2) Date: Jul. 9, 2018

(87) PCT Pub. No.: WO2018/074756
PCT Pub. Date: Apr. 26, 2018

(65) Prior Publication Data
US 2019/0021770 A1 Jan. 24, 2019

(30) Foreign Application Priority Data
Oct. 21, 2016 (KR) .......................... 10-2016-0137415

(51) Int. Cl.
*A61B 17/70* (2006.01)
*A61B 17/86* (2006.01)

(52) U.S. Cl.
CPC .......... *A61B 17/7035* (2013.01); *A61B 17/70* (2013.01); *A61B 17/7032* (2013.01);
(Continued)

(58) Field of Classification Search
CPC ....................................... A61B 17/7032–7046
See application file for complete search history.

(56) References Cited

U.S. PATENT DOCUMENTS

| 8,636,785 B2 | 1/2014 | Hes et al. |
| 2004/0102781 A1* | 5/2004 | Jeon .................. A61B 17/7032 606/916 |

(Continued)

FOREIGN PATENT DOCUMENTS

| KR | 10-2006-0035643 A | 4/2006 |
| KR | 10-2011-0073283 A | 6/2011 |

(Continued)

*Primary Examiner* — Nicholas J Plionis
(74) *Attorney, Agent, or Firm* — Novick, Kim & Lee, PLLC; Jae Youn Kim (57) ABSTRACT

Provided are a bone fixation screw apparatus and a fastening method thereof. More particularly, provided are a bone fixation screw apparatus and a fastening method thereof including a bone screw which is inserted to a lower side of a receiving portion and has a spherical head formed at a proximal end, a collect chuck which is inserted to an upper side of the receiving portion to be connected with the spherical head of the bone screw inside the receiving portion, and a rod which is seated on an upper side of the collet chuck and fixed through a fixing screw fastened to the receiving portion, in which the bone screw and the collet chuck are introduced to the receiving portion in opposite directions to each other. Therefore, it is possible to firmly and easily fasten the bone screw and the collet chunk and prevent the bone screw from being easily separated by external force.

16 Claims, 8 Drawing Sheets

(52) U.S. Cl.
CPC ...... *A61B 17/7037* (2013.01); *A61B 17/8685* (2013.01); *A61B 17/863* (2013.01)

(56) References Cited

U.S. PATENT DOCUMENTS

| | | | | |
|---|---|---|---|---|
| 2004/0267264 | A1* | 12/2004 | Konieczynski | A61B 17/7032 606/289 |
| 2007/0233078 | A1* | 10/2007 | Justis | A61B 17/7035 606/279 |
| 2007/0233122 | A1* | 10/2007 | Denis | A61B 17/7032 606/247 |
| 2010/0234902 | A1* | 9/2010 | Biedermann | A61B 17/7032 606/305 |
| 2011/0152949 | A1* | 6/2011 | Biedermann | A61B 17/7037 606/305 |
| 2012/0136395 | A1* | 5/2012 | Biedermann | A61B 17/7037 606/279 |
| 2013/0131734 | A1* | 5/2013 | Longtain | A61B 17/7037 606/305 |
| 2013/0338721 | A1* | 12/2013 | Biedermann | A61B 17/7037 606/305 |
| 2015/0080960 | A1* | 3/2015 | Biedermann | A61B 17/7037 606/278 |
| 2015/0142059 | A1* | 5/2015 | Biedermann | A61B 17/7037 606/266 |
| 2016/0361096 | A1* | 12/2016 | van der Pol | A61B 17/7076 |
| 2018/0014858 | A1* | 1/2018 | Biester | A61B 17/7037 |

FOREIGN PATENT DOCUMENTS

| | | |
|---|---|---|
| KR | 10-2012-0056215 A | 6/2012 |
| KR | 10-2015-0066158 A | 6/2015 |

* cited by examiner

BONE FIXATION SCREW APPARATUS AND FASTENING METHOD THEREOF

TECHNICAL FIELD

The present invention relates to a bone fixation screw apparatus and a fastening method thereof, and more particularly, to a bone fixation screw apparatus and a fastening method thereof capable of easily fastening a bone screw by inserting the bone screw to the lower side of a receiving portion and inserting a collet chuck to the upper side of the receiving portion and preventing the bone screw from being easily separated by external force by forming variable pitch screw threads at a proximal portion and a distal portion of the bone screw.

BACKGROUND ART

In general, a bone fixation screw apparatus is commonly used in orthopedics, neurosurgery, and the like to physically correct or fix the spine while being connected between adjacent vertebrae. A spin fixation procedure using the bone fixation screw apparatus is performed by a method of inserting a plurality of bone screws into the vertebrae, respectively, and connecting and fixing a rod disposed approximately in parallel to a longitudinal direction of the spine with the respective bone screws.

Such a bone fixation screw apparatus includes a bone screw insertable to the spine and a 'U'-shaped receiving portion in which the rod is received. The bone screw may be provided as a single screw fixed to the receiving portion or a multi-axis screw capable of freely moving with respect to the receiving portion.

In use, when the bone screw is screwed onto the spine and the bone screw is accurately disposed, the rod is installed in each receiving portion to connect the bone screws. Thereafter, the rod is fixed by a fastening mechanism such as a fixing screw, a plug, or a similar form.

However, in a conventional bone fixation screw apparatus, deformation frequently occurs between the bone screw implanted in the bone and the receiving portion such that the bone screw is not firmly fixed and the stability is poor.

Further, the conventional bone fixation screw apparatus has a problem in that there is a technical limitation that a collet chuck or the bone screw having an outer diameter relatively larger than an inner diameter of the receiving portion is inserted together to one side of the receiving portion.

In addition, in the conventional bone fixation screw apparatus, since the bone screw has a single screw thread without considering the anatomical characteristics of the bone, there is a problem in that the bone screw is easily separated by the external force when the bone screw is implanted into the bone.

Accordingly, the need for the bone fixation screw apparatus is gradually increasing to firmly fix the bone screw to the receiving portion, easily fasten the collet chuck and the bone screw to the receiving portion, and prevent the bone screw from being easily separated by the external force when the bone screw is implanted into the bone.

The above information disclosed in the background art is only for enhancement of understanding of the background of the present invention and therefore, it should not be construed as the related art that is already known in the related art to those skilled in the art.

DISCLOSURE

Technical Problem

The present invention is contrived to solve the problems in the related art described above, and an object of the present invention is to provide a bone fixation screw apparatus and a fastening method thereof capable of firmly and easily fastening a bone screw and a collet chuck to the inside of a receiving portion by inserting the bone screw from the lower side of the receiving portion and inserting the collet chuck into the upper side of the receiving portion.

Another object of the present invention is to provide a bone fixation screw apparatus and a fastening method thereof capable of preventing the bone screw from being easily separated by the external force by forming a proximal portion of the bone screw to be denser than a distal portion thereof.

Other technical objects desired to be achieved in the present invention are not limited to the aforementioned technical objects, and other technical objects which are not described above will be apparent to those skilled in the art from the disclosure of the present invention.

Technical Solution

In order to achieve the above objects, an exemplary embodiment of the present invention provides a bone fixation screw apparatus including: a bone screw which is inserted to a lower side of a receiving portion and has a spherical head formed at a proximal end; a collect chuck which is inserted to an upper side of the receiving portion to be connected with the spherical head of the bone screw inside the receiving portion; and a rod which is seated on an upper side of the collet chuck and fixed through a fixing screw fastened to the receiving portion, in which the bone screw and the collet chuck are introduced to the receiving portion in opposite directions to each other.

The bone fixation screw apparatus may further include a plurality of protrusions which protrude from an outer circumferential surface of the collet chuck; and a plurality of restraint grooves which are recessed on an inner circumferential surface of the receiving portion, in which the protrusions of the collet chuck may be inserted to the restraint grooves of the receiving portion to prevent the movement of the bone screw and the collet chuck.

When the collet chuck is introduced into the receiving portion, the protrusions of the collet chuck and the restraint grooves of the receiving portion may be oriented at predetermined angular intervals.

The bone fixation screw apparatus may further include a first tapered surface which is formed on a lower outer circumferential surface of the collet chuck and has a predetermined inclination angle toward the inside thereof; and a second tapered surface which is formed on a lower inner circumferential surface of the receiving portion and has a predetermined inclination angle toward the inside thereof.

An inclination angle of the first tapered surface and an inclination angle of the second tapered surface may be the same as or different from each other, and when the collect chuck is introduced to the receiving portion, the first tapered surface and the second tapered surface may be completely in surface contact or line contact with each other.

The bone fixation screw apparatus may further include a plurality of cutout portions which are perforated in the outer circumferential surface of the collet chuck so that the collet chuck is plastically deformed.

The cutout portions may be extended in a lateral direction along the outer circumferential surface of the collet chuck.

The bone fixation screw apparatus may further include a seating groove which is formed on the upper side of the collet chuck and covers one side of the rod.

The bone fixation screw apparatus may further include a rotation prevention groove which is recessed on the outer circumferential surface of the collet chuck; and a plastic deformation portion which is formed on the inner circumferential surface of the receiving portion and plastically deformed by external force to be introduced to the rotation prevention groove.

A plurality of protrusions may be formed on the outer circumferential surface of the collet chuck and the rotation prevention groove may be formed at a position where the protrusions are formed on the collet chuck.

The bone screw may include a proximal portion adjacent to the spherical head and a distal portion which is relatively more spaced apart from the spherical head than the proximal portion, and a screw thread formed on the proximal portion and a screw thread formed on the distal portion may be different from each other.

The screw thread formed on the proximal portion may be relatively denser than the screw thread formed on the distal portion.

A pitch of the screw thread formed on the proximal portion may be ½ of the pitch of the screw thread formed on the distal portion.

A valley diameter of the bone screw may gradually increase toward the proximal portion from the distal portion.

Another exemplary embodiment of the present invention provides a fastening method of a bone fixation screw including steps of: inserting a spherical head formed at a proximal end of a bone screw into a lower side of a receiving portion; inserting a collet chuck to an upper side of the receiving portion to connect the spherical head of the bone screw and the collet chuck to each other inside the receiving portion; inserting a plurality of protrusions formed on an outer circumferential surface of the collet chuck into a plurality of restraint grooves formed on an inner circumferential surface of the receiving portion to fix the collet chuck and the bone screw to the receiving portion; and seating a rod on an upper side of the collet chuck and fastening a fixing screw to the inside of the receiving portion to fix the rod.

In the connecting of the spherical head of the bone screw and the collet chuck, protrusions of the collet chuck and restraint grooves of the receiving portion may be oriented at predetermined angular intervals, and in the fixing of the collet chuck and the bone screw to the receiving portion, the protrusion of the collet chuck may rotate toward the restraint groove to be inserted into the restraint groove.

In the fixing of the collet chuck and the bone screw to the receiving portion, a first tapered surface formed on a lower outer circumferential surface of the collet chuck to have a predetermined inclination angle toward the inside thereof and a second tapered surface formed on a lower inner circumferential surface of the receiving portion to have a predetermined inclination angle toward the inside thereof may be completely in surface contact or line contact with each other.

The fastening method may further include introducing a plastic deformation portion to a rotation prevention groove formed on the outer circumferential surface of the collet chuck by applying external force to the plastic deformation portion formed on the inner circumferential surface of the receiving portion.

Advantageous Effects

According to the present invention having the above configuration, the bone screw is inserted to the lower side of the receiving portion and the collet chuck is inserted to the upper side of the receiving portion so as to connect the bone screw and the collet chuck to each other inside the receiving portion, thereby more easily fastening the bone fixation screw by a user.

Further, according to the present invention, the collet chuck or the bone screw having an outer diameter larger than the inner diameter of the receiving portion is not inserted to one side of the receiving portion, but the collet chuck and the bone screw are introduced to the receiving portion in opposite directions to each other, and thus, the deformation of the receiving portion does not occur.

Further, according to the present invention, the collet chuck and the receiving portion are fixed using the protrusions formed in the collet chuck and the restraint grooves formed in the receiving portion, the first tapered surface of the collet chuck is completely in surface contact or line contact with the second tapered surface of the receiving portion, and the movement of the bone screw is restrained by using the cutout portions, thereby firmly and stably connecting the bone screw and the receiving portion.

Finally, according to the present invention, the proximal portion is denser than the distal portion by considering the anatomical shape of the bone, thereby preventing the bone screw from being easily separated by the external force.

BEST MODE OF THE INVENTION

The present invention provides a bone fixation screw apparatus including: a bone screw which is inserted to a lower side of a receiving portion and has a spherical head formed at a proximal end; a collect chuck which is inserted to an upper side of the receiving portion to be connected with the spherical head of the bone screw inside the receiving portion; and a rod which is seated on an upper side of the collet chuck and fixed through a fixing screw fastened to the receiving portion, in which the bone screw and the collet chuck are introduced to the receiving portion in opposite directions to each other.

MODES OF THE INVENTION

The present invention will be described more fully hereinafter with reference to the accompanying drawings, in which exemplary embodiments of the invention are shown. However, the present invention can be realized in various different forms, and is not limited to the exemplary embodiments described herein.

In order to clearly describe the present invention, portions which are not related to the description will be omitted. Like reference numerals designate like or similar components throughout the specification.

Terms or words used in this specification and claims should not be interpreted as being limited to typical or dictionary meanings, but should be interpreted as having meanings and concepts which comply with the technical spirit of the present disclosure, based on the principle that an inventor can appropriately define the concept of the term to describe his/her own invention in the best manner.

Figure 1:
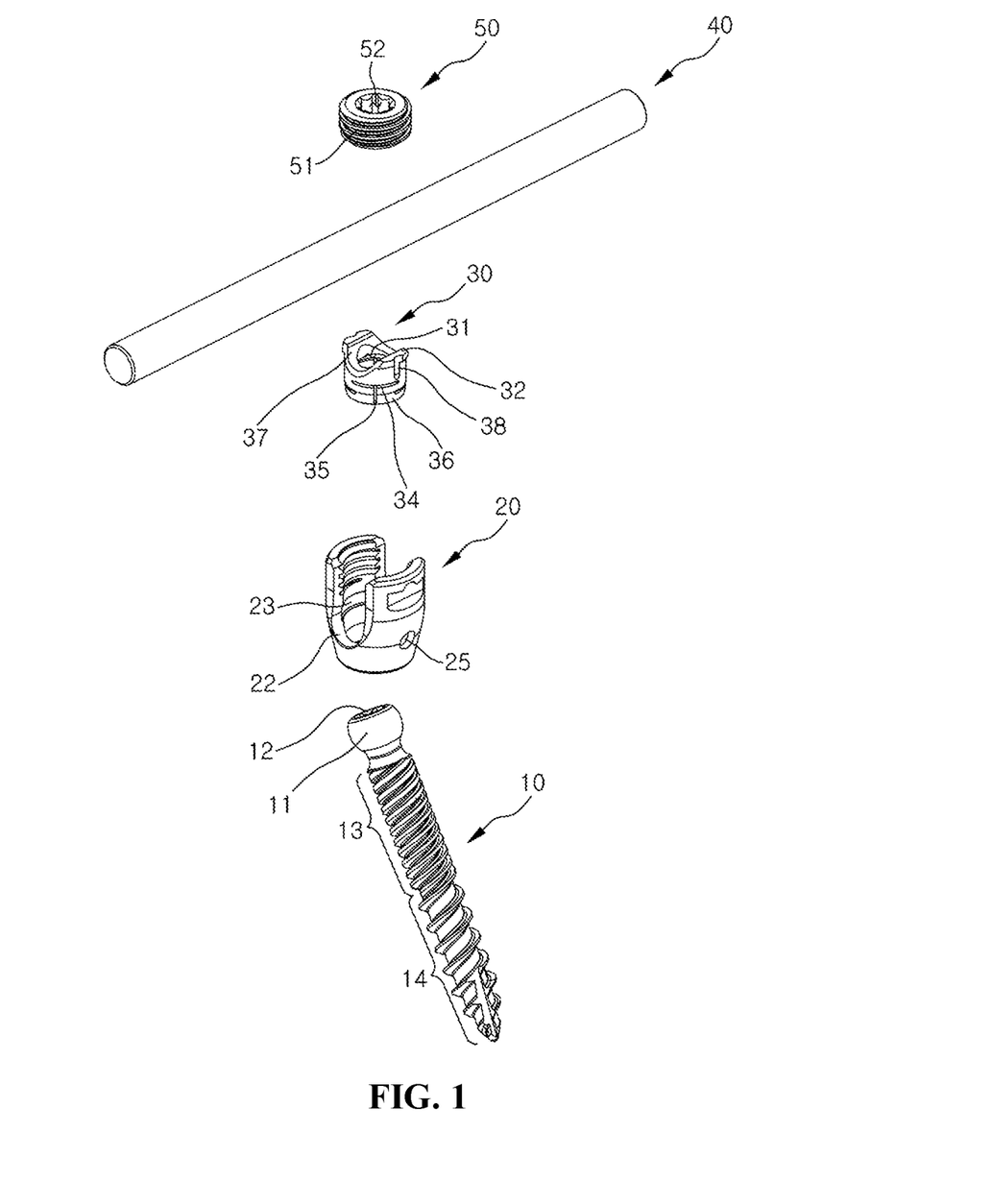
FIG. 1 is an exploded perspective view illustrating an appearance of a bone fixation screw apparatus according to an exemplary embodiment of the present invention.
Figure 2:
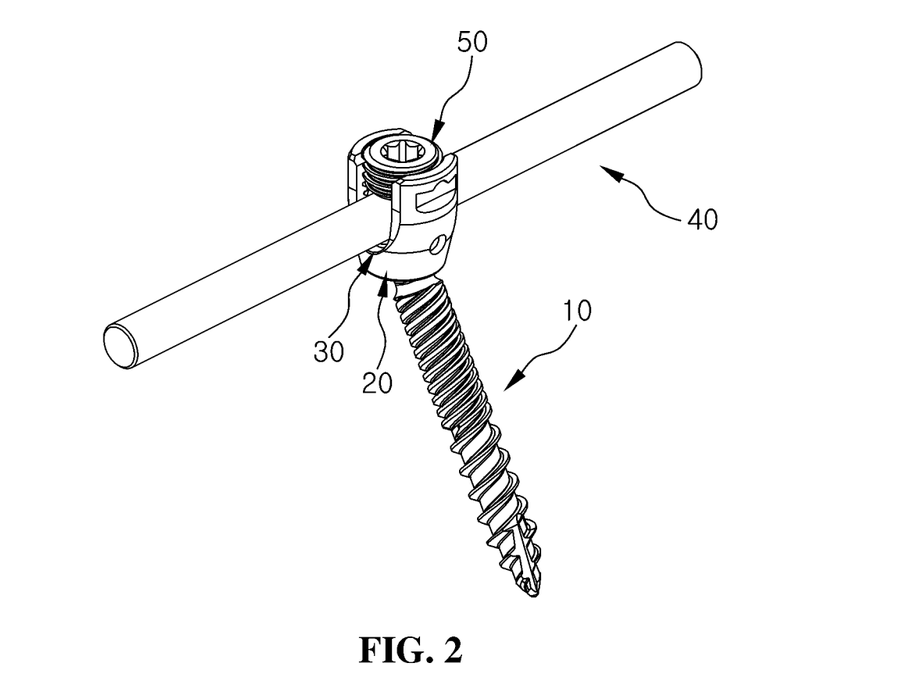
FIG. 2 is an assembly perspective view illustrating an appearance of the bone fixation screw apparatus according to the exemplary embodiment of the present invention.
Figure 3:
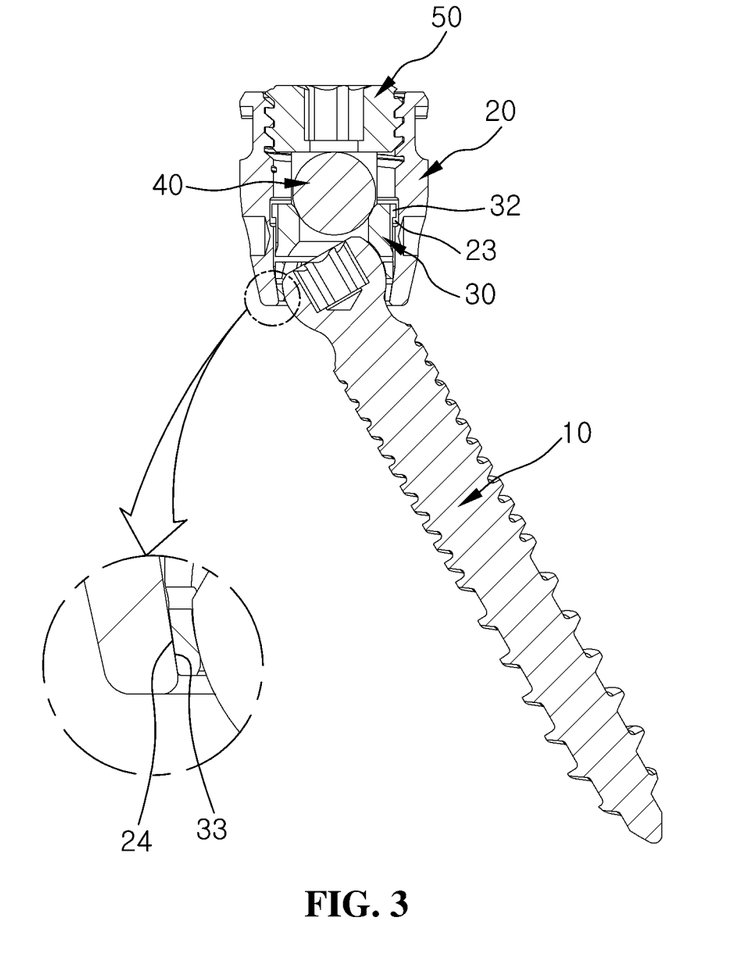
FIG. 3 is a diagram illustrating a cross section of the bone fixation screw apparatus illustrated in FIG. 2.

FIG. 1 is an exploded perspective view illustrating an appearance of a bone fixation screw apparatus according to an exemplary embodiment of the present invention, FIG. 2 is an assembly perspective view illustrating an appearance of the bone fixation screw apparatus according to the exemplary embodiment of the present invention, and FIG. 3 is a diagram illustrating a cross section of the bone fixation screw apparatus illustrated in FIG. 2.

As illustrated in the drawings, a bone fixation screw apparatus according to an exemplary embodiment of the present invention includes a bone screw 10 having predetermined length and diameter, a collet chuck 30 inserted to a receiving portion 20 to fix the bone screw, a rod 40 seated on the upper side of the collet chuck to connect the bone fixation screw apparatuses to each other, and a fixing screw 50 fastened to the inside of the receiving portion to fix the rod.

The bone screw 10 has a screw thread formed on an outer circumferential surface to be inserted to the bone and a spherical head 11 formed on a proximal end (the upper end in the drawing) in various shapes such as a cut-out sphere, an elliptical sphere, or an egg shape. The spherical head 11 has a tool groove 12 to which a working tool is inserted to rotate the bone screw.

The receiving portion 20 has opened upper and lower sides so that the spherical head 11 of the bone screw 10, the collet chuck 30, the rod 40 and the fixing screw 50 may be received. A female screw portion 21 is formed on the upper side of the receiving portion 20 so that the fixing screw 50 may be fastened, and U-shaped through grooves 22 are formed on both sides thereof so that the rod 40 passes through.

The collet chuck 30 has a length and a diameter that may be inserted into the receiving portion 20 and has an introduction hole 31 formed at the center thereof so that the spherical head 11 of the bone screw 10 may be inserted and fixed inward.

The fixing screw 50 has a male screw portion 51 formed on the outer circumferential surface so as to be fastened to the female screw portion 21 of the receiving portion 20 and a tool groove 52 formed at the upper end thereof so that a working tool is inserted to rotate the fixing screw like the spherical head.

As described below, a user completes the assembly by inserting the bone screw 10 into the lower side of the receiving portion 20, inserting the collet chuck 30 to the upper side of the receiving portion 20, connecting the bone screw 10 and the collet chuck 30 to each other inside the receiving portion 20, rotating the collet chuck 30 so that the collect chuck 30 is fixed to the receiving portion 20, and then connecting the rod 40 and the fixing screw 50 to the upper portion of the collet chuck 30.

Figure 4:
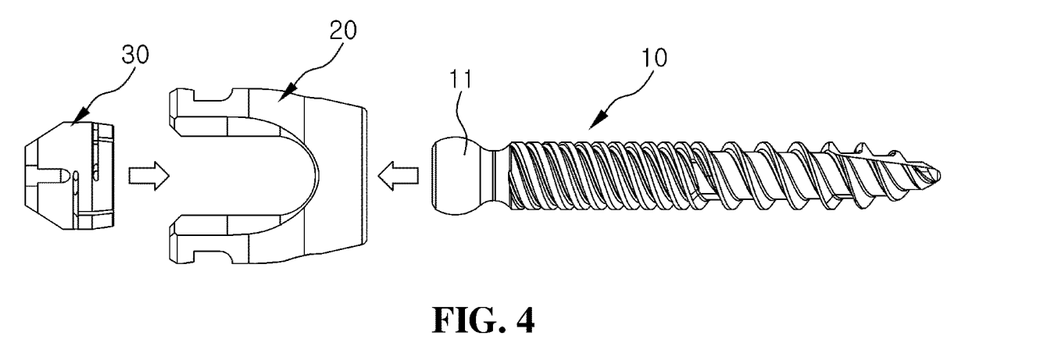
FIG. 4 is a diagram illustrating an appearance in which a bone screw and a collet chuck are introduced into a receiving portion according to the exemplary embodiment of the present invention.
Figure 5A:
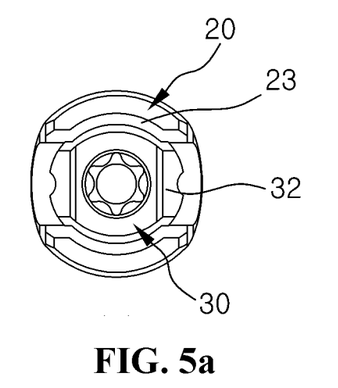
FIGS. 5a and 5b are diagrams illustrating an appearance in which the bone screw and the collet chuck are introduced into the receiving portion to be connected to each other at the inside of the receiving portion according to the exemplary embodiment of the present invention.
Figure 5B:
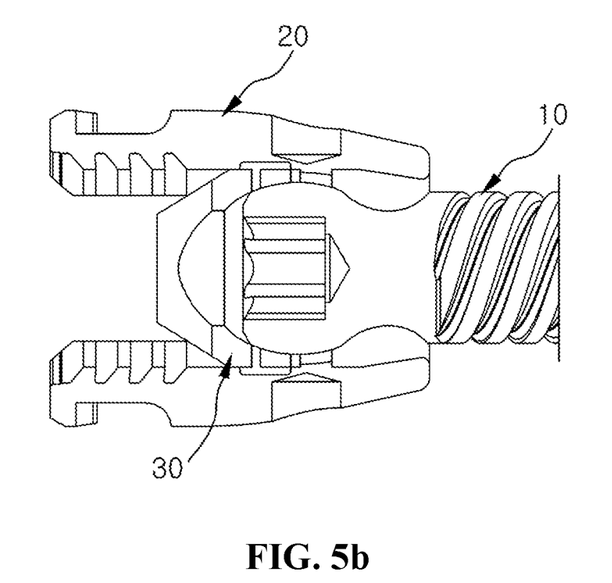
Figure 6A:
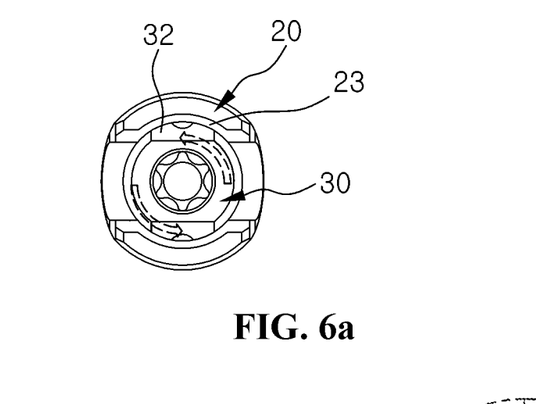
FIGS. 6a and 6b are diagrams illustrating an appearance in which the collet chuck is connected to the receiving portion according to the exemplary embodiment of the present invention.
Figure 6B:
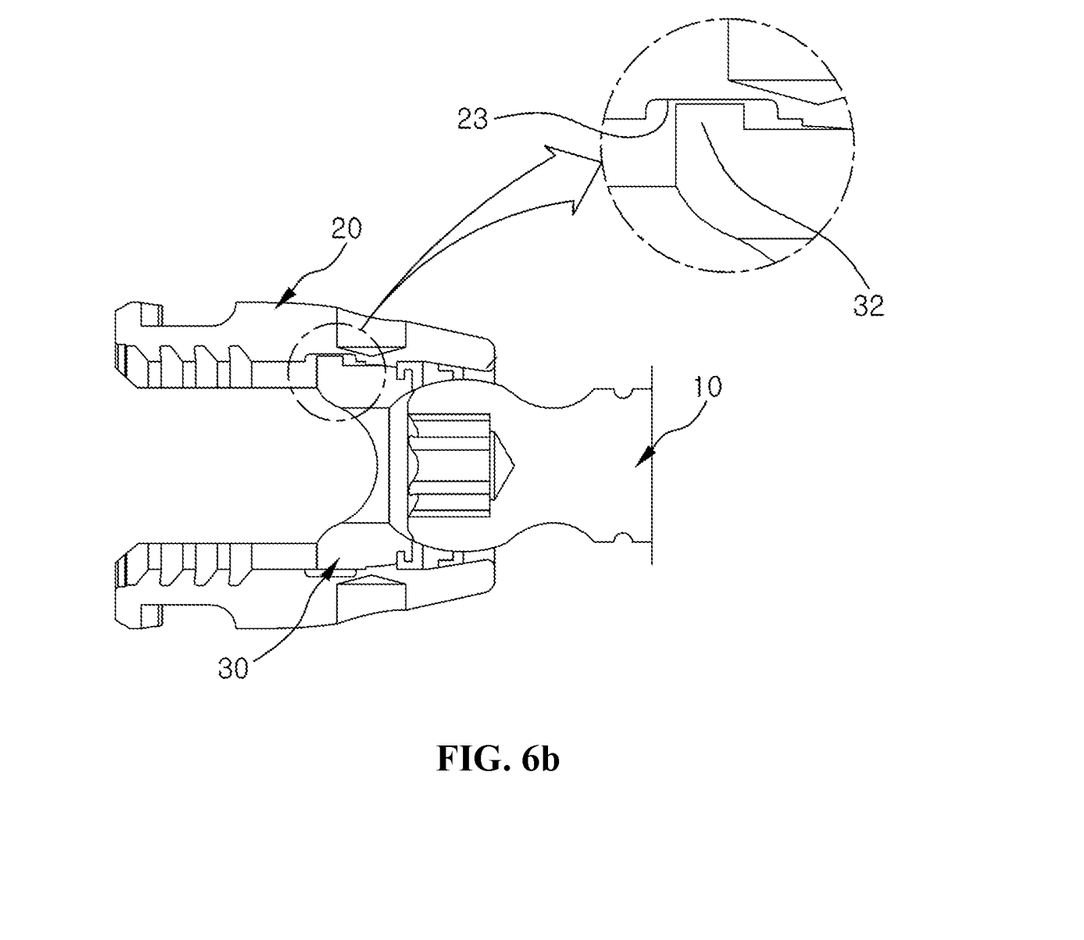

FIG. 4 is a diagram illustrating an appearance in which a bone screw and a collet chuck are introduced into a receiving portion according to the exemplary embodiment of the present invention, FIGS. 5a and 5b are diagrams illustrating an appearance in which the bone screw and the collet chuck are introduced into the receiving portion to be connected to each other at the inside of the receiving portion according to the exemplary embodiment of the present invention, and FIGS. 6a and 6b are diagrams illustrating an appearance in which the collet chuck is connected to the receiving portion according to the exemplary embodiment of the present invention.

Particularly, FIG. 5a is a plan view illustrating an appearance in which the bone screw 10 and the collet chuck 30 are introduced to the receiving portion 20 to be connected to each other inside the receiving portion 20 according to the exemplary embodiment of the present invention, and FIG. 5b is a cross-sectional view illustrating an appearance of the bone screw 10 and the collet chuck 30 illustrated in FIG. 5a. FIG. 6a is a plan view illustrating an appearance in which the collet chuck 30 is connected to the receiving portion 20 according to the exemplary embodiment of the present invention, and FIG. 6b is a cross-sectional view illustrating an appearance of the collet chuck 30 and the receiving portion 20 illustrated in FIG. 6a.

As illustrated in FIG. 4, the bone screw 10 according to the present invention is introduced to the receiving portion from the lower side (the right side in the drawing) of the receiving portion 20, and the collet chuck 30 is introduced to the receiving portion from the upper side (the left side in the drawing) of the receiving portion 20.

In a conventional bone fixation screw apparatus, the bone screw and the collet chuck are connected to each other and then introduced to the upper side or the lower side of the receiving portion, but there is a difference in that the bone screw 10 and the collet chuck 30 according to the present invention are introduced to the receiving portion 20 in opposite directions to each other.

This may be achieved because the conventional bone fixation screw apparatus prevents the collet chuck from being separated by adjusting the size of the upper and lower opened portions of the receiving portion, whereas in the present invention, the bone fixation screw apparatus prevents the collet chuck 30 from being separated by protrusions 32 and restraint grooves 23 to be described below.

Accordingly, according to the present invention, there is an advantage in that deformation of the receiving portion does not occur in the process of inserting the bone screw 10 and the collet chuck 30 into the receiving portion 20, and the bone screw and the collet chuck are more firmly and stably fixed.

As illustrated in FIGS. 1, 5a, 5b, 6a and 6b, a plurality of protrusions 32 is formed to protrude from the outer circumferential surface of the collet chuck 30 and a plurality of restraint grooves 23 is formed to be recessed on the inner circumferential surface of the receiving portion 20 to be inserted with the protrusions 32.

As illustrated in FIGS. 5a and 5b, when the collet chuck 30 is introduced to the inside of the receiving portion 20 or when the collet chuck 30 and the bone screw 10 are initially connected to each other, the protrusions 32 of the collet chuck and the restraint grooves 23 of the receiving portion are oriented at predetermined angular intervals. For example, the protrusions 32 and the restraint grooves 23 may be oriented at 90° intervals.

That is, the user may fix the collet chuck 30 and the bone screw 10 to the inside of the receiving portion 20 by introducing the collet chuck to the receiving portion so that the protrusions 32 of the collet chuck 30 are oriented toward the through grooves 22 of the receiving portion 20 and then rotating the collet chuck 30 at a predetermined angle as illustrated in FIGS. 6a and 6b to insert the protrusions 32 into the restraint grooves 23.

In addition, as illustrated in FIG. 3, a first tapered surface 33 having a predetermined inclination angle toward the inside thereof may be formed on a lower outer circumferential surface of the collet chuck 30, and a second tapered surface 24 having a predetermined inclination angle toward the inside thereof may be formed on a lower inner circumferential surface of the receiving portion 20.

The first tapered surface 33 formed in the collet chuck 30 and the second tapered surface 24 formed in the receiving portion 20 press the lower end of the collet 30 inward to prevent the bone screw 10 from being separated from the collet chuck 30 and fix the bone screw at a predetermined angle at the same time.

In this case, the inclination angle of the first tapered surface 33 and the inclination angle of the second tapered surface 24 are the same as or different from each other, and when the collet chuck 30 is introduced to the receiving portion 20, the first tapered surface 33 and the second tapered surface 24 may be completely in surface contact or line contact with each other.

That is, when the user connects the collet chuck 30 and the bone screw 10 inside the receiving portion 20 and then pushes and rotates the collet chuck below the receiving portion so that the protrusions 32 are inserted to the restraint grooves 23, the first tapered surface 33 is completely in surface contact or line contact with the second tapered surface 24 and pressed inward, and in this process, the bone screw is fixed.

Meanwhile, as illustrated in FIG. 1, a plurality of cutout portions 34 is formed on the outer circumferential surface of the collet chuck 30. The cutout portions 34 are extended in a lateral direction along the outer circumferential surface of the collet chuck 30 and may communicate with a dividing portion 35 perforated in a longitudinal direction in the collet chuck 30. In the illustrated exemplary embodiment, the cutout portion 34 and the dividing portion 35 are orthogonal to each other to form a 'T' shape as a whole, but in some cases, it will be understood to those skilled in the art that the cutout portion 34 and the dividing portion 35 may have various shapes such as a 'Y' shape, an arrow shape in which the cutout portion is bent downward, a shape in which the cutout portion is diagonally disposed, and a shape in which the cutout portion is bent.

The dividing portion 35 divides the lower end of the collet chuck 30 into a plurality of dividing ends 36, the plurality of dividing ends 36 is extended and deployed when the spherical head 11 of the bone screw 10 is connected to the collet chuck 30, and the collect chuck is elastically deformed when the collet chuck 30 is pressed by the rod 40, thereby improving the connection strength such that the cutout portion 34 restrains the movement of the bone screw.

The cutout portions 34 may be disposed on the outer circumference surface of the collet chuck 30 to have various heights, but in the illustrated exemplary embodiment, one cutout portion 34 has a zigzag height with the adjacent cutout portions, thereby more improving the connection strength.

A seating groove 37 may be formed at the upper side of the collet chuck 30 to cover one side (a lower side in the drawing) of the rod 40. The seating groove 37 is formed in a spherical surface and has an effect of preventing the movement of the rod.

Figure 7:
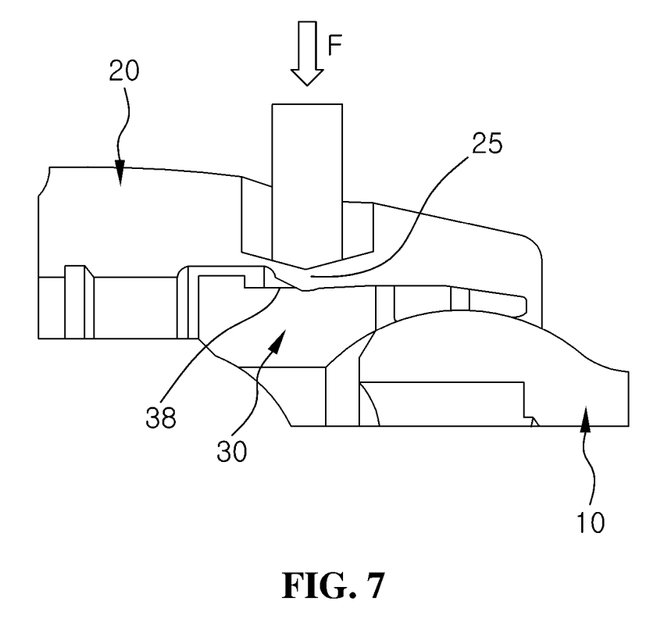
FIG. 7 is an enlarged cross-sectional view illustrating an appearance of a rotation prevention groove and a plastic deformation portion according to the exemplary embodiment of the present invention.

FIG. 7 is an enlarged cross-sectional view illustrating an appearance of a rotation prevention groove and a plastic deformation portion according to the exemplary embodiment of the present invention.

As illustrated in FIGS. 1 and 7, a rotation prevention groove 38 is recessed on the outer circumferential surface of the collet chuck 30, and a plastic deformation portion 25 which is plastically deformed by external force F to be introduced to the rotation prevention groove 38 is formed on the inner circumferential surface of the receiving portion 20.

The rotation prevention groove 38 is formed in a vertical direction (longitudinal direction) of the collet chuck at a position where the protrusions 32 of the collet chuck 30 are formed, and the plastic deformation portion 25 is introduced to the rotation prevention groove 38 to prevent the axial rotation of the collet chuck.

Figure 8:
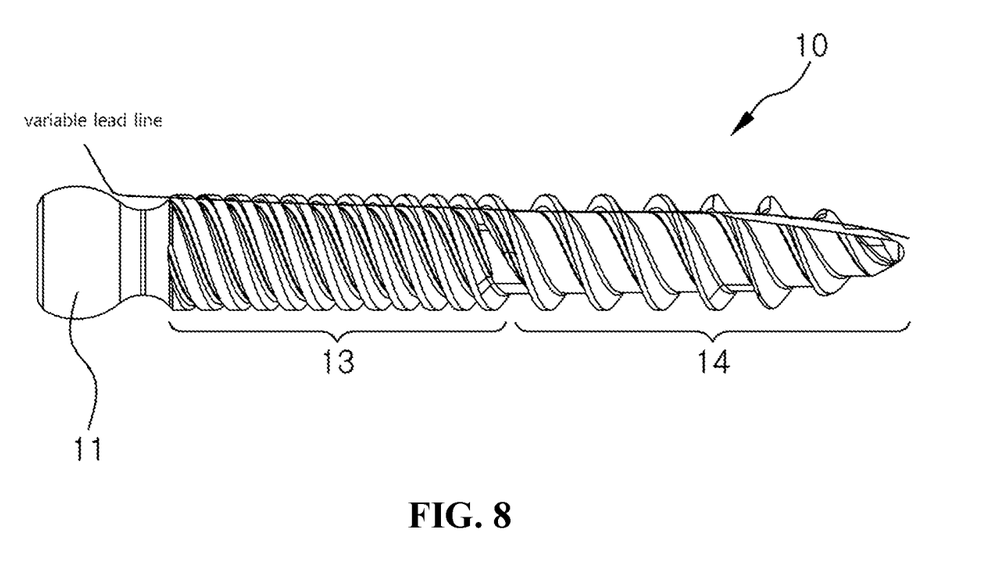
FIG. 8 is a configuration diagram illustrating an appearance of the bone screw according to the exemplary embodiment of the present invention.

FIG. 8 is a configuration diagram illustrating an appearance of the bone screw according to the exemplary embodiment of the present invention.

As illustrated in FIG. 8, the bone screw 10 includes a proximal portion 13 adjacent to the spherical head 11 and a distal portion 14 disposed to be relatively more spaced apart from the spherical head than the proximal portion. A screw thread formed on the proximal portion 13 and a screw thread formed on the distal portion 14 are different from each other, and the screw thread formed on the proximal portion 13 is relatively denser than the screw thread formed on the distal portion 14.

That is, the bone screw 10 may have a variable pitch according to the anatomical shape of the bone to be inserted. When the bone screw 10 is inserted into the bone, the proximal portion 13 is located in a dense bone having a relatively high bone density and the distal portion 14 is located in a cancellous bone having a relatively low bone density.

Specifically, the screw thread formed on the proximal portion 13 is formed of a quadruple screw thread, and the screw thread formed on the distal portion 14 is formed of a double screw thread. In other words, a pitch of the screw thread formed on the proximal portion 13 is ½ of the pitch of the screw thread formed on the distal portion 14. In the bone screw 10, four screw threads of the proximal portion 13 are arranged with the same length and two screw threads of the distal portion 14 are arranged with the same length.

In addition, the bone screw 10 has a variable lead line of which a valley diameter (a virtual cylindrical diameter contacting the valley bottom of the male screw) gradually increases toward the proximal portion 13 from the distal portion 14.

Accordingly, when the bone screw 10 according to the present invention is implanted into the bone, the bone screw 10 may not be easily separated by the external force and firmly and stably fixed to the implanted bone.

A fastening method of the bone fixation screw according to the exemplary embodiment of the present invention will be described below.

The fastening method of the bone fixation screw according to the present invention includes steps of inserting the spherical head 11 formed at a proximal end of the bone screw 10 into the lower side of the receiving portion 20, inserting the collet chuck 30 to the upper side of the receiving portion 20 to connect the spherical head 11 of the bone screw 10 and the collet chuck 30 to each other inside the receiving portion 20, inserting a plurality of protrusions 31 formed on the outer circumferential surface of the collet chuck 30 into a plurality of restraint grooves 23 formed on the inner circumferential surface of the receiving portion 20 to fix the collet chuck 30 and the bone screw 10 to the receiving portion 20, and seating the rod 40 on the upper side of the collet chuck 30 and fastening the fixing screw 50 to the inside of the receiving portion 20 to fix the rod 40.

As illustrated in FIG. 4, in the conventional bone fixation screw, the bone screw and the collet chuck are introduced in one direction of the receiving portion, whereas the bone screw 10 according to the present invention is introduced to the lower side of the receiving portion 20 and the collet chuck 30 is introduced to the upper side of the receiving portion 20 to be connected with the bone screw 10 inside the receiving portion 20.

Accordingly, according to the present invention, there is an advantage in that the deformation of the receiving portion does not occur in the process of inserting the bone screw 10 and the collet chuck 30 into the receiving portion 20, and the bone screw and the collet chuck are more firmly and stably fixed.

At this time, as illustrated in FIGS. 5a and 5b, a plurality of protrusions 32 formed in the collet chuck 30 is oriented at predetermined angular intervals with a plurality of restraint grooves 23 formed in the receiving portion 20. Thereafter, as illustrated in FIGS. 6a and 6b, the collet chuck 30 rotates by a predetermined angle toward the restraint grooves 23 such that the protrusions 32 are inserted to the restraint grooves 23.

As illustrated in FIG. 3, when the collet chuck 30 and the bone screw 10 are fixed to the receiving portion 20, the first tapered surface 33 formed on the lower outer circumferential surface of the collet chuck 30 is completely in surface contact or line contact with the second tapered surface 24 formed on the lower inner circumferential surface of the receiving portion 20.

The lower end of the collet chuck 30 is pressed inward by the first tapered surface 33 and the second tapered surface 24 to prevent the bone screw from being separated from the collet chuck and fix the bone screw at a predetermined angle.

Thereafter, as illustrated in FIG. 7, the external force F is applied to the plastic deformation portion 25 formed on the inner circumferential surface of the receiving portion 20, and the plastic deformation portion 25 is introduced to the rotation prevention groove 38 formed on the outer circumferential surface of the collet chuck 30 to prevent the axial rotation of the collet chuck.

The present invention having the configuration and the fastening method described above has an advantage in that the bone screw 10 is inserted to the lower side of the receiving portion 30 and the collet chuck 30 is inserted to the upper side of the receiving portion 20 so as to connect the bone screw 10 and the collet chuck 30 to each other inside the receiving portion 20, thereby more easily fastening the bone fixation screw by the user.

Further, according to the present invention, the collet chuck or the bone screw having an outer diameter larger than the inner diameter of the receiving portion is not inserted to one side of the receiving portion, but the collet chuck 30 and the bone screw 10 are introduced to the receiving portion 20 in opposite directions to each other, and thus, the deformation of the receiving portion does not occur.

Further, according to the present invention, the collet chuck 30 and the receiving portion 20 are fixed using the protrusions 32 formed in the collet chuck 30 and the restraint grooves 23 formed in the receiving portion 20, the first tapered surface 33 of the collet chuck 30 is completely in surface contact or line contact with the second tapered surface 24 of the receiving portion 20, and the movement of the bone screw 10 is restrained by using the cutout portions 34, thereby firmly and stably connecting the bone screw and the receiving portion.

Finally, according to the present invention, the proximal portion 13 is denser than the distal portion 14 by considering the anatomical shape of the bone, thereby preventing the bone screw 10 from being easily separated by the external force.

The aforementioned present invention is not limited to the aforementioned exemplary embodiments and the accompanying drawings, and it will be obvious to those skilled in the technical field to which the present invention pertains that various substitutions, modifications, and changes may be made within the scope without departing from the technical spirit of the present invention.

The invention claimed is:

1. A bone fixation screw apparatus comprising:
    a receiving portion having an opened upper end and an opened lower end;
    a bone screw having a spherical head disposed at a proximal end thereof, wherein the spherical head of the bone screw is configured to be inserted into the opened lower end of the receiving portion;
    a collect chuck configured to be inserted into the opened upper end of the receiving portion and to be connected with the spherical head of the bone screw inside the receiving portion; and
    a rod configured to be seated on an upper side of the collet chuck and fixed through a fixing screw fastened to the receiving portion,
    wherein the collet chuck includes a plurality of slots perforated in a lateral direction along an outer circumferential surface thereof and a plurality of dividing slots perforated in a longitudinal direction of the outer circumferential surface thereof, and each of the plurality of slots communicates with corresponding each of the plurality of dividing slots such that the corresponding each of the plurality of diving slots and the each of the plurality of slots are orthogonal to each other to form a "T" shape,
    wherein the plurality of slots are disposed at differing zigzag heights from the respective adjacent slots,
    wherein the plurality of dividing slots divide a lower end of the collet chuck into a plurality of dividing ends, the plurality of dividing ends is extended and deployed around the spherical head of the bone screw when the spherical head is connected to the collet chuck, and the collet chuck is elastically deformed when the collet chuck is pressed by the rod, such that the plurality of slots and dividing slots restrain a movement of the bone screw, and wherein the bone screw and the collet chuck are inserted into the receiving portion in opposite directions to each other.

2. The bone fixation screw apparatus of claim 1, wherein a plurality of protrusions are disposed on the outer circumferential surface of the collet chuck, wherein a plurality of restraint grooves are recessed on an inner circumferential surface of the receiving portion, and wherein each of the plurality of protrusions of the collet chuck are configured to be inserted to corresponding each of the plurality of restraint grooves of the receiving portion to prevent the movement of the bone screw and the collet chuck.

3. The bone fixation screw apparatus of claim 2, wherein when the collet chuck is inserted into the receiving portion, the plurality of protrusions of the collet chuck and the plurality of restraint grooves of the receiving portion are oriented at predetermined angular intervals.

4. The bone fixation screw apparatus of claim 1, wherein a first tapered surface is disposed on a lower outer circumferential surface of the collet chuck and has a first predetermined inclination angle toward an inside thereof; and wherein a second tapered surface is disposed on a lower inner circumferential surface of the receiving portion and has a second predetermined inclination angle toward an inside thereof.

5. The bone fixation screw apparatus of claim 4, wherein the first predetermined inclination angle of the first tapered surface and the second predetermined inclination angle of the second tapered surface are the same as or different from each other, and when the collect chuck is inserted into the receiving portion, the first tapered surface and the second tapered surface are completely in surface contact or line contact with each other.

6. The bone fixation screw apparatus of claim 1, wherein the upper side of the collet chuck includes a seating groove configured to cover one side of the rod.

7. The bone fixation screw apparatus of claim 1, wherein a rotation prevention groove is recessed on the outer circumferential surface of the collet chuck, and wherein a plastic deformation portion is disposed on an inner circumferential surface of the receiving portion and is configured to be plastically deformed when an external force is introduced to the rotation prevention groove.

8. The bone fixation screw apparatus of claim 7, wherein a plurality of protrusions are disposed on the outer circumferential surface of the collet chuck and the rotation prevention groove is recessed at a position adjacent to where the plurality of protrusions are disposed on the collet chuck.

9. The bone fixation screw apparatus of claim 1, wherein the bone screw includes a proximal portion adjacent to the spherical head and a distal portion which is relatively more spaced apart from the spherical head than the proximal portion, and
a screw thread disposed on the proximal portion and a screw thread disposed on the distal portion are different from each other.

10. The bone fixation screw apparatus of claim 9, wherein the screw thread disposed on the proximal portion is relatively denser than the screw thread disposed on the distal portion.

11. The bone fixation screw apparatus of claim 9, wherein a pitch of the screw thread disposed on the proximal portion is ½ of a pitch of the screw thread disposed on the distal portion.

12. The bone fixation screw apparatus of claim 9, wherein a valley diameter of the bone screw gradually increases toward the proximal portion from the distal portion.

13. A fastening method of a bone fixation screw, the method comprising:
inserting a spherical head disposed at a proximal end of a bone screw into a receiving portion, wherein the receiving portion has an opened upper end and the opened lower end and the spherical head is inserted into the opened lower end of the receiving portion;
inserting a collet chuck to the opened upper end of the receiving portion to connect the spherical head of the bone screw and the collet chuck to each other inside the receiving portion;
inserting a plurality of protrusions disposed on an outer circumferential surface of the collet chuck into a plurality of restraint grooves recessed on an inner circumferential surface of the receiving portion to fix the collet chuck and the bone screw to the receiving portion; and
seating a rod on an upper side of the collet chuck and fastening a fixing screw to an inside of the receiving portion to fix the rod,
wherein the collet chuck includes a plurality of slots perforated in a lateral direction along an outer circumferential surface thereof and a plurality of dividing slots perforated in a longitudinal direction of the outer circumferential surface thereof, and each of the plurality of slots communicates with corresponding each of the plurality of dividing slots such that the corresponding each of the plurality of diving slots and the each of the plurality of slots are orthogonal to each other to form a "T" shape,
wherein the plurality of slots are disposed at differing zigzag heights from the respective adjacent slots,
wherein the plurality of dividing slots divide a lower end of the collet chuck into a plurality of dividing ends, the plurality of dividing ends is extended and deployed around the spherical head of the bone screw when the spherical head is connected to the collet chuck, and the collet chuck is elastically deformed when the collet chuck is pressed by the rod, such that the plurality of slots and dividing slots restrain a movement of the bone screw.

14. The fastening method of claim 13, wherein in the inserting of the plurality of protrusions into the plurality of restraint grooves, the plurality of protrusions of the collet chuck and the plurality of restraint grooves of the receiving portion are oriented at predetermined angular intervals, and
each of the plurality of protrusions of the collet chuck are rotated toward each of the plurality of restraint grooves to be inserted into the each of the plurality of restraint grooves.

15. The fastening method of claim 13, wherein after the inserting of the plurality of protrusions to the plurality of restraint grooves, a first tapered surface disposed on a lower outer circumferential surface of the collet chuck to have a first predetermined inclination angle toward an inside thereof and a second tapered surface disposed on a lower inner circumferential surface of the receiving portion to have a second predetermined inclination angle toward an inside thereof are completely in surface contact or line contact with each other.

16. The fastening method of claim 13, further comprising:
introducing a plastic deformation portion to a rotation prevention groove recessed on the outer circumferential surface of the collet chuck by applying an external force to the plastic deformation portion disposed on the inner circumferential surface of the receiving portion.

* * * * *